United States Patent
Chol et al.

(10) Patent No.: US 7,629,006 B2
(45) Date of Patent: Dec. 8, 2009

(54) PROCESS FOR PREPARING EXTRACT FROM RHUS VERNICIFLUA AND PHARMACEUTICAL COMPOSITION CONTAINING THE SAME

(75) Inventors: Won-Cheol Chol, Incheon (KR); Sang-Jae Park, Yongin-si (KR); Sung-Pil Kwon, Seoul (KR)

(73) Assignee: AZI Company, Ltd, Gangwon-do (KR)

( * ) Notice: Subject to any disclaimer, the term of this patent is extended or adjusted under 35 U.S.C. 154(b) by 388 days.

(21) Appl. No.: 11/570,495

(22) PCT Filed: Sep. 8, 2005

(86) PCT No.: PCT/KR2005/002976

§ 371 (c)(1), (2), (4) Date: Dec. 12, 2006

(87) PCT Pub. No.: WO2006/043752

PCT Pub. Date: Apr. 27, 2006

(65) Prior Publication Data

US 2008/0233223 A1  Sep. 25, 2008

(30) Foreign Application Priority Data

Sep. 9, 2004  (KR) .................. 10-2004-0071944

(51) Int. Cl.
*A61K 36/00* (2006.01)

(52) U.S. Cl. .................................. 424/725

(58) Field of Classification Search ........... None
See application file for complete search history.

(56) References Cited

U.S. PATENT DOCUMENTS 3,819,726 A * 6/1974 Khurana ............... 568/753
4,198,496 A * 4/1980 Halasa et al. ........... 526/115

FOREIGN PATENT DOCUMENTS

| KR | 1020010070556 | 7/2001 |
|----|---------------|--------|
| KR | 1020010111159 | 12/2001 |
| KR | 1020020002096 | 1/2002 |
| KR | 1020020004800 | 1/2002 |
| KR | 1020030079255 | 10/2003 |
| KR | 1020040079397 | 9/2004 |

OTHER PUBLICATIONS

Coley et al. (Epidemiologic Reviews (2008), vol. 30, pp. 35-66).*
Translation of KR 2001-0111159-2001.*
Lim, K.T. et al. "Antioxidative effects of Ethanol extracts from Rhus Verniciflua Stokes (RVS) on mouse whole brain cells" In; Korean J. Food Sci. Technol. 1997;29(6):1248-54.
Kitts, et al. "Antitumorigenic and cytotoxic properties of an ethanol extract derived from Rhus Verniciflua Stokes (RVS)" In; J. Toxicol. Environ. Health A 2001; 64(4):357-71.

* cited by examiner

*Primary Examiner*—Susan C Hoffman
(74) *Attorney, Agent, or Firm*—AKC Patents LLC; Aliki K. Collins

(57) ABSTRACT

The present invention provides a process for preparing an extract of *Rhus verniciflua* by using water and organic solvents to extract active ingredients, which comprises (a) adding water or a mixture of water and alcohol as the solvent to *Rhus verniciflua* to extract the soluble components, then filtering the resultant product to obtain a filtrate, and concentrating and drying the filtrate to obtain a solid fraction; (b) re-extracting the solid fraction obtained in the previous step with highly purified ethanol, then filtering the resultant product to obtain a filtrate, and concentrating and drying the filtrate to obtain a solid fraction; (c) adding a saturated hydrocarbon having 5 to 7 carbon atoms to the solid fraction obtained in the previous step to dissolve allergy-inducing components, and then removing the hydrocarbon to obtain a solid fraction; and (d) adding water to the solid fraction obtained in the previous step to extract water-soluble components. The extract obtained according to the process for preparing an extract of *Rhus verniciflua* of the invention does not induce allergies, since toxic substances of lacquer are effectively removed, and various inherent active ingredients of lacquer can be extracted with high yield, compared with conventional processes.

12 Claims, 2 Drawing Sheets

Saline Administered/ Aβ(40-1) injected    Saline Administered/ Aβ(1-42) injected    Extract Administered/ Aβ(1-42) injected Saline Administered/
Aβ(40-1) injected Saline Administered/
Aβ(1-42) injected Extract
Administered/
Aβ(1-42) injected

PROCESS FOR PREPARING EXTRACT FROM RHUS VERNICIFLUA AND PHARMACEUTICAL COMPOSITION CONTAINING THE SAME

TECHNICAL FIELD

The present invention relates to a process for preparing an extract from *Rhus verniciflua* and a pharmaceutical composition containing the extract. More particularly, the invention relates to a process for preparing an extract from *Rhus verniciflua*, in which active ingredients of *Rhus verniciflua* can be obtained with high yield, as compared with conventional methods of thermally treating the *Rhus* plant at high temperatures or repeating extraction and fractionation so as to remove allergy-inducing materials from lacquer, and in which a mixture of water and alcohol, a highly purified alcohol, a saturated hydrocarbon and water are used as the solvent during the processes of extracting the *Rhus* plant and drying the extract, in order to give a *Rhus verniciflua* extract having the inherent pharmacological efficacy of the *Rhus* plant without causing allergies; and a pharmaceutical composition for memory enhancement which contains the extract as the active ingredient.

BACKGROUND ART

*Rhus verniciflua* (or *Rhus vernicifera*) is a deciduous tree belonging to the Anacardiaceae family. This plant is indigenous to the Central Asian highlands and Himalayan regions, and is currently distributed throughout the world, particularly in the subtropical regions including the tropical regions and also in the temperate regions. The plant is cultivated in the Northeast Asian region including Korea, Japan and China, mainly for the purpose of obtaining lacquer.

The sap of *Rhus verniciflua* is referred to as lacquer, and dried lacquer has been traditionally known in the Oriental medicine to have the functions of removing extravasated blood, promoting blood circulation and having efficacy against intestinal worms, abdominal pain, hyperacidity, coughs, tuberculosis, amenorrhea, constipation, diabetes mellitus, malaria and the like. Recently, dried lacquer has been reported to have an anticancer effect (Namba, T., Colored Illustrations of Wakan Yaku. p 215, Hoikusha Publishing Co. Ltd., Osaka, 1980).

In Korea, *Rhus verniciflua* has been used in special dishes for restorative or medicinal purposes, such as lacquer chickens, lacquer ducks and the like. Furthermore, the sap of the *Rhus* plant has useful properties such as durability which makes the plant to be used as a natural coating material, and chemical resistance which makes the plant to be used as a special exterior coating material for aircraft, ships, submarine optic cables and the like.

However, a person who is highly sensitive to lacquer may suffer from dermatitis (allergies) even upon brief contact with lacquer, and thus most people tend to avoid contacting with lacquer. In fact, the ratio of the population showing no sensitive responses against lacquer is only about 20 to 40%.

The component in lacquer which induces allergy as such is urushiol, which is one of the main components of the sap of *Rhus verniciflua*. The component is a dark brown liquid used in lacquerwork, and it is highly soluble in organic solvents. The principal chemical structures of urushiol include side chains having 15 to 17 carbon atoms, with a number of unsaturated bonds being present in the chains. Urushiol itself is a strong allergy causing material and that is the major restriction in obtaining pharmacological effect from the intake of the extract.

The main components that are reported to exhibit the pharmacological efficacy of *Rhus verniciflua* are urushiol, fustin, fisetin, sulforetin, butein and the like, and studies have been made on the compositions based on these components and functions thereof.

The main pharmacological actions of lacquer that are known include the anticancerous and antioxidative actions, the hangover-curing action and the like (Korean J. Food Sci. Technol., 31, 238-245 (1997)). In addition, lacquer is known to have efficacy against gastric diseases, heart diseases, arthritis, hypertension, diabetes, stroke, arthritis, chronic fatigue and the like.

Despite such various pharmacological actions, lacquer has not been commercialized yet because of its toxicity to human body. Therefore, there is a strong demand for a method which can provide the maximal pharmacological efficacy of *Rhus verniciflua*, and which can minimize allergies upon intake of the *Rhus* plant or an extract thereof, from the perspective of commercializing the plant or the extract.

Heretofore, as the process for preparing an extract of *Rhus verniciflua* while removing its toxicity, disclosed are a process for preparing *Rhus verniciflua* health beverages by adding alder tree components (see Korean Patent Application Publication No. 2001-0035052); and a process for preparing beverages by boiling *Rhus verniciflua* in water together with pine leaves, mulberry roots, Amomi semen and the like (Korean Patent Application Publication No. 1995-0023317). These processes involve merely boiling the *Rhus* plant together with other added materials to reduce the toxicity of the *Rhus* plant. Thus, the processes could not sufficiently eliminate toxicity and thus, hardly succeeded in commercializing the *Rhus* extract.

Furthermore, a process involving fractionation (Korean Patent Application Publication No. 2002-0002096), a process involving leaving an ethanol extract of the plant to stand for a length of time (Korean Patent Application Publication No. 2003-0079255) and the like, use column chromatography as a final process to extract active ingredients and to eliminate toxicity. Thus, there are problems such as complicated process, lengthened processing time and high costs.

In addition to these, heat treatment techniques have been suggested, such as a process for eliminating toxicity through the steps of hot air drying and solvent extraction (Korean Patent Application Publication No. 2002-0023439) and a process for removing toxic substances by heat treatment (Korean Patent No. 0394089). However, these processes involve heat treatment at a high temperature ranging from 100 to 400° C., and thus, may cause side effects such as destruction of the active ingredients that are thermally labile.

Meanwhile, techniques for extracting specific active ingredients of *Rhus verniciflua* and uses thereof have been suggested as described below. Most of these techniques have been developed with focusing on the extraction of components such as urushiol, fustin, fisetin and the like.

Examples of such techniques include: New use of urushiol derivatives as an anti-cancer medicine including anti-oxidative activity and method of preparation thereof (Korean Patent Application Publication No. 1997-0013163 and Korean Patent No. 0215390); a manufacturing method of extract of *Rhus verniciflua* STOKES having high antioxidant activity (Korean Patent Application Publication No. 2003-0079255); use of an extract of *Rhus verniciflua* having inhibitory effects of reverse transcriptase (Korean Patent Application Publication No. 2002-0084333); a hepatoprotective composition comprising an extract of *Rhus verniciflua* having fustin, fisetin, sulfuretin, butein and the like as main components (Korean Patent Application Publication No. 2002-0077833); a liver disease treating agent containing the extract and flavonoid compounds isolated from *Rhus verniciflua* STOKES (Korean Patent Application Publication No. 2004-0043255); and the like, and extraction and separation of the above-described components were usually carried out using silica columns.

DISCLOSURE OF THE INVENTION

Technical Problem

Therefore, the present invention is intended to solve the aforementioned problems of the prior arts and conventional technical problems.

Thus, it is an object of the invention to provide a novel process for preparing an extract of *Rhus verniciflua* which does not cause allergies, wherein the active ingredients of *Rhus verniciflua* can be obtained with high yield while completely removing the allergy-inducing components, by repeating extraction with a series of specific solvents and drying, unlike conventional processes of utilizing high temperature heat treatment, extraction, fractionation and silica column chromatography.

It is another object of the invention to provide an extract prepared as described above, and a pharmaceutical composition containing the extract which is effective for memory enhancement and treatment of dementia.

Solutions to the Technical Problems

The process for preparing an extract of *Rhus verniciflua* according to the invention is a process using water and organic solvents to extract the active ingredients of the *Rhus* plant, which comprises:

(a) adding water or a mixture of water and alcohol as the solvent to *Rhus verniciflua* to extract the soluble components, then filtering the resultant product to obtain a filtrate, and concentrating and drying the filtrate to obtain a solid fraction;

(b) re-extracting the solid fraction obtained in the previous step with highly purified ethanol, then filtering the resultant product to obtain a filtrate, and concentrating and drying the filtrate to obtain a solid fraction;

(c) adding a saturated hydrocarbon having 5 to 7 carbon atoms to the solid fraction obtained in the previous step to remove the allergy-inducing components by dissolving, and then filtering out the hydrocarbon to obtain a solid fraction; and (d) adding water to the solid fraction obtained in the previous step to extract water-soluble components.

The feature of the invention is that in the process of eliminating the toxicity of *Rhus verniciflua*, the toxic substances can be completely removed by repeated processes of extraction using appropriately selected solvents and drying, instead of using the conventionally used column chromatography technique.

Another feature of the invention is that, unlike the conventional processes involving heat treatment at high temperatures, there is no direct heating step, and extraction does not require a high temperature condition. Thus, there occurs no loss of the thermally labile ingredients, and the inherent pharmacologically active ingredients of *Rhus verniciflua* can be extracted without being damaged.

Hereinafter, the preparation process of the invention will be described in more detail, with description of each of the steps as follows.

First, in step (a), water or a mixture of water and alcohol is added to *Rhus verniciflua* to extract the soluble components. The *Rhus* plant is preferably used in a finely cut state. Any alcohol can be miscible with water may be used, but ethanol among them is particularly preferred. The content of the alcohol is 0 to 90% by volume with respect to water, and the amount of water and alcohol used may be 3 to 15 weight-folds with respect to the *Rhus* plant. When the amount of the solvent is too small, there is a problem that extraction is not sufficiently achieved so that the yield is lowered. When the amount of the solvent is too large, there is a problem that too long a time is required for concentrating and drying the extract. The extraction temperature is preferably in the range of 30 to 100° C., and the temperature is elevated to the above range in order to increase the extraction yield and to reduce the duration for extraction. After the extraction, the insolubles are removed by filtration. The obtained liquid extract may contain various soluble components and some of the urushiol which is known to exhibit the toxicity of *Rhus verniciflua*. Thus, an additional step for removing this urushiol component is needed. The extract obtained after filtration is concentrated in a vacuum for complete removal of the solvent, thus to give a solid fraction which is used in the next step.

In step (b), the solid fraction obtained in the step (a) is subjected to extraction by adding a highly purified ethanol solvent thereto. Here, it is preferable to use a highly purified ethanol having a purity of 95 to 99.9% (v/v), in an amount of 3 to 30 weight-folds with respect to the solid fraction. This step is carried out so as to remove polymeric materials such as polysaccharides, which are highly soluble in an aqueous solvent, but hardly soluble in high purity ethanol. Accordingly, it is essential to remove water completely upon concentration in the step (a). In the presence of any residual water, the concentration of ethanol may be lowered, and the ethanol-insoluble components also may be re-extracted during the process of re-extraction with ethanol. After the step of extraction with ethanol, the insoluble components are removed by filtration, and the obtained filtrate is concentrated in vacuo to remove the solvent. In this process, too, the ethanol solvent should be removed completely, such that the concentration of residual ethanol should be 1% or less. When ethanol remains at this concentration or above, it will be mixed with the hydrocarbon used in the next step, and the ethanol-soluble components will be transferred to the hydrocarbon layer and removed, thus the yield being lowered.

In step (c), a saturated $C_5$-$C_7$ hydrocarbon is added to the solid fraction obtained in the step (b) to elute the components that are soluble in the hydrocarbon, which are then removed by filtration. Here, the hydrocarbon is used to extract not the final desired product but the substances that need to be removed. That is, the substances soluble in the hydrocarbon are components such as urushiol, which cause side effects such as inducing allergy when taken in. Urushiol can be dissolved in a hydrocarbon which is immiscible with water and then removed. Among the hydrocarbons, saturated hydrocarbons having 5 to 7 carbon atoms are preferably used, and hexane is more preferred. The hydrocarbon can be added in an amount of 1 to 30 weight-folds with respect to the solid fraction. As this step is described with reference to the case of using hexane for example, urushiol-type compounds present in the solid fraction are eluted with hexane, making the hexane yellowish in color. When the yellowish hexane is removed by filtration, the urushiol-type compounds are washed away with hexane and removed. After the filtration, any hexane remaining in the precipitate is completely evaporated to give a solid fraction, which is used in the next step.

In step (d), a process of extraction with water is carried out to extract out water-soluble components from the solid fraction obtained in the step (c). Water can be added in an amount of 1 to 50 weight-folds with respect to the solid fraction, with which a number of extraction operations can be carried out in a controlled amount or frequency. After the extraction with water, any water-insoluble precipitates are removed by filtration. The precipitates are nearly black in color and are easily removed by filtration.

Preferably, an additional step of adding alumina to the filtrate obtained in the step (d) to completely remove allergy-inducing components by adsorption, filtering the resulting mixture, and then concentrating and freeze-drying the filtrate obtained therefrom, can be carried out.

The filtrate obtained by the process of extraction with water in the step (d) is wine-colored. Alumina is added thereto in an amount of 1 to 10% (w/v) by volume of the filtrate, and the mixture is stirred at 20 to 50° C. for 1 to 5 hours. During this process, other allergy-inducing substances and insoluble components are adsorbed to the alumina and removed completely, thus the finally obtained powder product may have higher solubility in water and ethanol. When the filtrate obtained after removing the added alumina by filtration is concentrated and then freeze-dried, a water soluble *Rhus verniciflua* extract is obtained in a powder form.

In some cases, other conventional processes can be further performed as long as the processes have no adverse influence on the effect of the invention, and such variances and modifications should be considered to be all included in the scope of the invention.

Furthermore, the invention provides an extract of *Rhus verniciflua* having a function of cerebral neural cell protection, which is prepared by the above-described process.

The extract according to the invention contains, as the main components, 1 to 30% by weight of fustin (3,3',4',7-tetrahydroxyflavanone), 0.5 to 20% by weight of fisetin (3,3',4',7-tetrahydroxyflavone), 0 to 5% by weight of sulfuretin (3',4',6-trihydroxyaurone) and 0 to 3% by weight of butein (3,4,2',4-tetrahydroxychalcone), which are flavonoid compounds. The chemical structures of these flavonoid compounds are as follows:

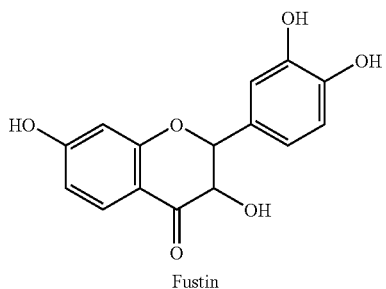
Fustin

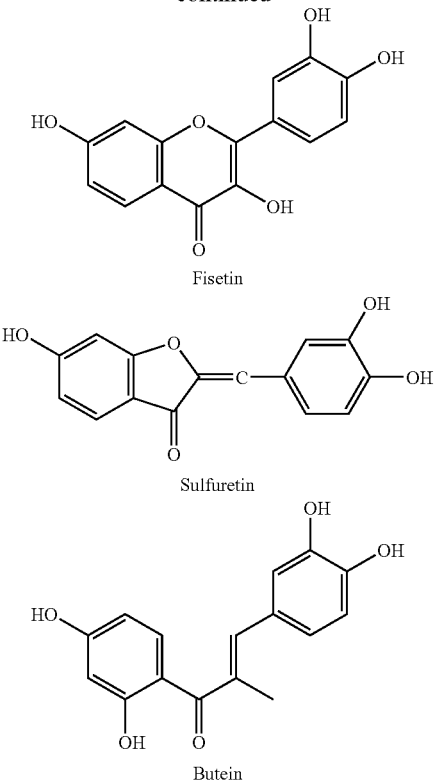
Fisetin

Sulfuretin

Butein

Other components in the extract include resins, water-soluble polysaccharides, saccharides and the like originating from *Rhus verniciflua*.

The composition and content of these components in the extract according to the invention may be significantly variable within a certain scope, since *Rhus verniciflua* is a natural material which may vary depending on the gathering region and season, and the gathered plant parts.

The extract has a cerebral neural cell protective function, and its effect in memory enhancement has been confirmed.

The invention also provides a pharmaceutical composition comprising (a) a therapeutically effective amount of the above-described extract as an active ingredient, and (b) a pharmaceutically acceptable carrier, diluent, excipient or a combination thereof.

The term "pharmaceutical composition" refers to a mixture of the extract of the invention and other chemical components such as a diluent and a carrier. The purpose of a pharmaceutical composition is to facilitate administration of a compound to an organism. There are many techniques for administering therapeutically active ingredients, including oral administration, injection, aerosol, parenteral administration, topical administration and the like, without being limited thereto.

The term "therapeutically effective amount" refers to an amount of the compound being administered sufficient to alleviate to some extent one or more of the symptoms of the disease being treated. Therefore, the therapeutically effective amount refers to an amount that has effects of: (1) reversing the progression of the disease; (2) inhibiting any further progression of the disease to some extent; and/or (3) relieving to some extent (preferably eliminating) one or more symptoms associated with the disease.

The term "carrier" refers to a compound that facilitates the incorporation of an active ingredient into cells or tissues. For example, dimethyl sulfoxide (DMSO) is a commonly utilized carrier as it facilitates the uptake of many organic compounds into the cells or tissues of an organism.

The term "diluent" refers to a chemical compound that stabilizes the biologically active form of the active ingredient and also is dilutable in water, which is to finally dissolve the active ingredient of interest. Salts dissolved in buffer solutions are utilized as diluents in the art. One commonly used buffer solution is phosphate buffer saline because it mimics the osmotic condition of human body fluids. Because buffer salts can control the pH of a solution at low concentrations, a diluent rarely modifies the biological activity of a compound.

The term "pharmaceutically acceptable" refers to a carrier or diluent that does not cause damage to the biological activity and properties of the active ingredient.

The extract according to the invention can be administered to a human patient per se, or in pharmaceutical compositions in which they are mixed with other active ingredients, as in combination therapy, or suitable carriers or excipients. Techniques for formulation and administration of the compounds of the instant application may be found in "Remington's Pharmaceutical Sciences", Mack Publishing Co., Easton, Pa., 18th edition (1990).

a) Routes of Administration

Suitable routes of administration may, for example, include oral, nasal, transmucosal, or intestinal administration; and parenteral delivery, including intramuscular, subcutaneous, intravenous, intramedullary injections, as well as intrathecal, direct intraventricular, intraperitoneal or intraocular injections.

b) Composition/Formulation

The pharmaceutical compositions of the invention may be manufactured in a manner that is known per se, e.g., by means of conventional mixing, dissolving, granulating, dragee-making, levigating, emulsifying, encapsulating, entrapping or lyophilizing processes.

Therefore, pharmaceutical compositions for use in accordance with the invention may be formulated in a conventional manner using one or more pharmaceutically acceptable carriers comprising excipients and auxiliaries that facilitate processing of the active compounds into preparations that can be used pharmaceutically. Suitable formulation is dependent upon the route of administration selected. Any one of known prior arts, carriers and excipients can be suitably used as understood in the art to which the invention pertains, for example, in the aforementioned Remingston's Pharmaceutical Sciences.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be easily formulated by combining the active ingredients with pharmaceutically acceptable carriers well known in the art. Such carriers enable the extract of the invention to be formulated as tablets, pills, dragees, capsules, liquids, gels, syrups, slurries, suspensions and the like. Pharmaceutical preparations for oral use can be obtained by mixing the extract of the invention with one or two or more excipients, optionally grinding a resulting mixture, and processing the mixture of granules, after adding suitable auxiliaries, if desired, to obtain tablets or dragee cores. Suitable excipients are, in particular, fillers such as lactose, sucrose, mannitol, or sorbitol; cellulose preparations such as, for example, corn starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as a cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycol or sorbitol. The push-fit capsules can contain the active ingredients in admixture with filler such as lactose, binders such as starches, and/or lubricants such as talc or magnesium stearate. In soft capsules, the active compounds may be dissolved or suspended in suitable liquids, such as fatty acids, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the extract according to the invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. Capsules and cartridges of for example, gelatin for use in an inhaler or insufflator may be formulated by containing a powder mixture of the compound and a suitable powder base such as lactose or starch.

The extract may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active ingredients in a water-soluble form. Additionally, suspensions of the active ingredients may be prepared as appropriate oily injection suspensions. Suitable lipophilic solvents or vehicles include fatty acids such as sesame oil, or synthetic fatty acid esters, such as ethyl oleate or triglycerides, or liposomes. Aqueous injection suspensions may contain substances that increase the viscosity of the suspension, such as sodium carboxymethylcellulose, sorbitol, or dextran. Optionally, the suspension may also contain stabilizers or agents that increase the solubility of the compounds to allow for the preparation of highly concentrated solutions.

Furthermore, the active ingredient may be in powder form for constitution with a suitable vehicle, e.g., sterile pyrogen-free water, before use.

The active ingredients may also be formulated in rectal compositions such as suppositories or retention enemas, e.g., containing conventional suppository bases such as cocoa butter or other glycerides.

A pharmaceutical carrier for the extract according to the invention is a cosolvent system comprising benzyl alcohol, a nonpolar surfactant, a water-miscible organic polymer, and an aqueous phase. The cosolvent system may be the VPD cosolvent system. VPD is a solution of 3% w/v of benzyl alcohol, 8% w/v of the nonpolar surfactant Polysorbate 80™, and 65% w/v of polyethylene glycol 300, made up to volume in absolute ethanol. The VPD cosolvent system (VPD:D5W) consists of VPD diluted 1:1 with a 5% dextrose in water solution. This cosolvent system dissolves hydrophobic compounds well, and itself produces low toxicity upon systemic administration. Naturally, the proportions of a cosolvent system may be varied considerably without destroying its solubility and toxicity characteristics. Furthermore, the identity of the cosolvent components may be varied: for example, other low-toxicity nonpolar surfactants may be used instead of Polysorbate 80™; the fraction size of polyethylene glycol may be varied; other biocompatible polymers may replace polyethylene glycol, e.g. polyvinylpyrrolidone; and other sugars or polysaccharides may substitute for dextrose.

Alternatively, other delivery systems may be employed. Liposomes and emulsions are well known examples of delivery vehicles for hydrophobic drugs. Certain organic solvents such as dimethylsulfoxide also may be employed, although usually at the cost of greater toxicity. Additionally, the active ingredients may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

c) Effective Dosage

Pharmaceutical compositions suitable for use in the invention include compositions where the active ingredients are contained in an amount effective to achieve its intended purpose. More specifically, a therapeutically effective amount means an amount of the compound effective to prevent, alleviate or ameliorate symptoms of the disease or prolong the survival of the subject being treated. Determination of the therapeutically effective amount is well within the capability of those skilled in the art, especially in light of the detailed disclosure provided herein.

For the extract according to the invention, the therapeutically effective dose can be estimated initially from cell culture assays. For example, a dose can be formulated in animal models to achieve a circulating concentration range that includes the $IC_{50}$ as determined in cell culture. Such information can be used to more accurately determine useful doses in humans.

The dosage may vary within this range depending upon the dosage form employed and the route of administration utilized. The exact formulation, route of administration and dosage can be chosen by the individual physician in view of the patient's condition. (See e.g., Fingl, et al. (1975), "The Pharmacological Basis of Therapeutics", Ch. 1 p. 1). Usually, a proper range of the composition dosage to be administered to the patient can be about 0.5 to 1000 mg/kg of the patient's weight. The dosage, according to the degree necessary for the patient, can be provided once or in a series of twice or more times per day or more.

In cases of local administration or selective uptake, the effective local concentration of the drug may not be related to plasma concentration.

The amount of the composition administered will, of course, be dependent on the subject being treated, on the subject's weight, the severity of the affliction, the manner of administration and the judgment of the prescribing physician.

Such pharmaceutical composition according to the invention can be preferably used as a composition for the prevention and treatment of dementia.

BEST MODE FOR CARRYING OUT THE INVENTION

Figure 1:
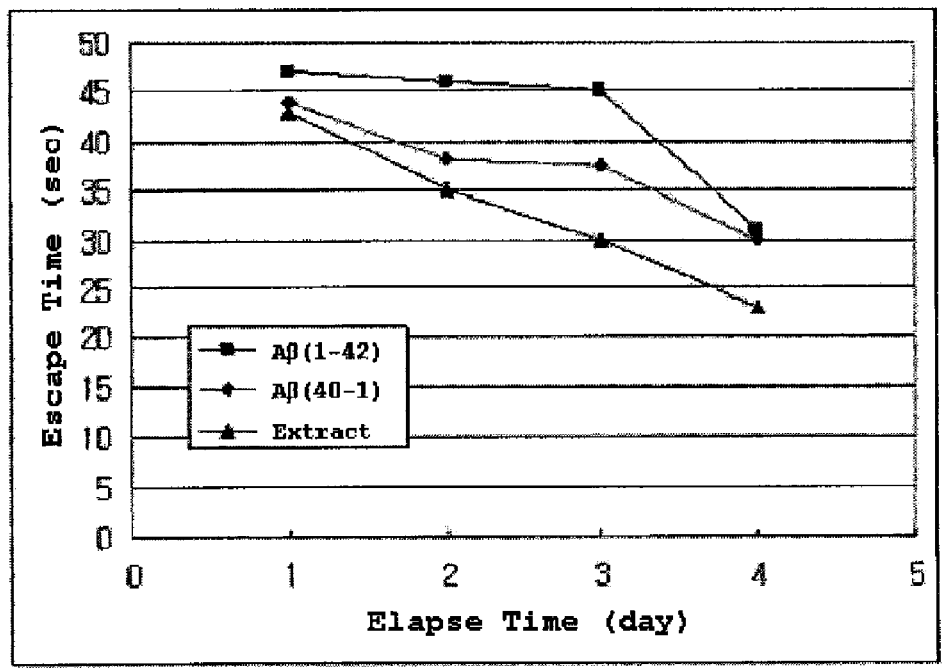
FIG. 1 is a graph showing the results of a hidden platform test according to Experimental Example 2.

Hereinafter, the present invention will be described in detail with reference to Examples and Experimental Examples, but the scope of the invention is not limited thereto.

EXAMPLE 1

Preparation of Extract 100 g of *Rhus verniciflua* was finely cut into a size of 1 cm or less, a 10-fold amount of water was added thereto, and the mixture was subjected to extraction at 60° C. for 12 hours. The extract was filtered using a filter paper to remove an insoluble solids, and 940 ml of a liquid extract was obtained. The liquid extract was concentrated to give 3.9 g of a solid fraction. 300 ml of 95% (v/v) purity ethanol was added thereto, and the mixture was subjected to extraction at 35° C. to dissolve ethanol-soluble components. Thereafter, the mixture was filtered to remove ethanol-insoluble substances, and 286 ml of an ethanol extract was obtained. The ethanol extract was concentrated, and the solvent was completely evaporated to give 3.1 g of a solid fraction. 100 ml of hexane was added thereto to wash away and remove hexane-soluble components. The amount of the remaining solid fraction was 3.0 g. 300 ml of water was added thereto to extract out components that are soluble in water. The extract was filtered to remove a residual solid fraction, and 290 ml of the wine-colored final liquid extract was obtained. 13 g of alumina was added to adsorb any impurities while stirring at 35° C. for 3 hours. The mixture was filtered to remove alumina and the like, and 280 ml of the filtrate was obtained, which was then concentrated to 110 ml. The concentrated filtrate was then freeze dried to yield 1.0 g of a yellow powder. The resulting powder did not contain urushiol, the toxic substance of *Rhus verniciflua*, and was a completely water-soluble material, being very highly soluble in water and ethanol.

The extract was analyzed, and it was found that the extract contained flavonoid compounds, namely, 19.3% (w/w) of fustin, 13.2% (w/w) of fisetin, 0.85% (w/w) of sulfuretin and 0.12% (w/w) of butein.

EXPERIMENTAL EXAMPLE 1

Allergy Inducing Test

The extract obtained in Example 1 was prepared into a 5% aqueous solution, and an allergy inducing test was carried out on 9 people with high sensitivity to *Rhus verniciflua*. The results are shown in the following Table 1.

TABLE 1

|  | 5$^{th}$ day | 10$^{th}$ day | 15$^{th}$ day |
|---|---|---|---|
| Spots(erythema) | 0 | 0 | 0 |
| Inflammation | 0 | 0 | 0 |

As can be seen from the Table 1, the extract of the invention did not induce allergies in any case.

EXPERIMENTAL EXAMPLE 2

Memory Enhancing Effect (Hidden Platform Test)

Using the extract obtained in Example 1, the memory enhancing effect was evaluated. The test was carried out according to the Morris water maze method using mice. For the test, the mice whose memory and learning ability were damaged by using beta-amyloid (Aβ), were used as a model. The extract obtained in Example 1 was administered to the mice, and the mice were subjected to comparison with the control group. The present experiment was a test for evaluating the reference memory and working memory, which are necessary for learning. Further tests on the memory enhancing effect were carried out in the following Experimental Example 3 and Experimental Example 4.

1) Treatment of mice: The mice were used for the test after adaptation for a week. At this stage, the extract of the invention was orally administered at a rate of 65 mg/kg every 12 hours. After 7 days and 6 hours from the last administration, 400 pmol each of beta-amyloids Aβ (1-42) and Aβ (40-1) were injected per mouse, which substances are known to impair memory and induce dementia. After 3 days from the time of injection, a hidden platform test was carried out for 4 days.

2) Test method: A platform was placed in a water maze below the water surface so that a mouse could not see the platform (so-called a hidden platform). In order to precisely locate the platform below the water surface, the mouse must accurately memorize the location of the platform and the direction and distance thereto in relation to the four different cues disposed in four different directions. During the 4-day experiment, five executions each day were repeated such that the starting position was changed each time so as to reduce the error. The time taken to reach the hidden platform from entrance to the maze was measured. The reference memory, also known as the long-term memory, is reported to be related to damages in the hippocampus of the brain.

3) Test results: The results are shown in FIG. 1. As can be seen from FIG. 1, after 3 days, the mice administered with the extract of the invention took relatively very short times to locate the platform under water, compared with the mice having no administration. From these results, it can be seen that the extract of the invention enhanced the memory of the mice and allowed preservation of the memory from the effect of the dementia-inducing substance.

Figure 2:
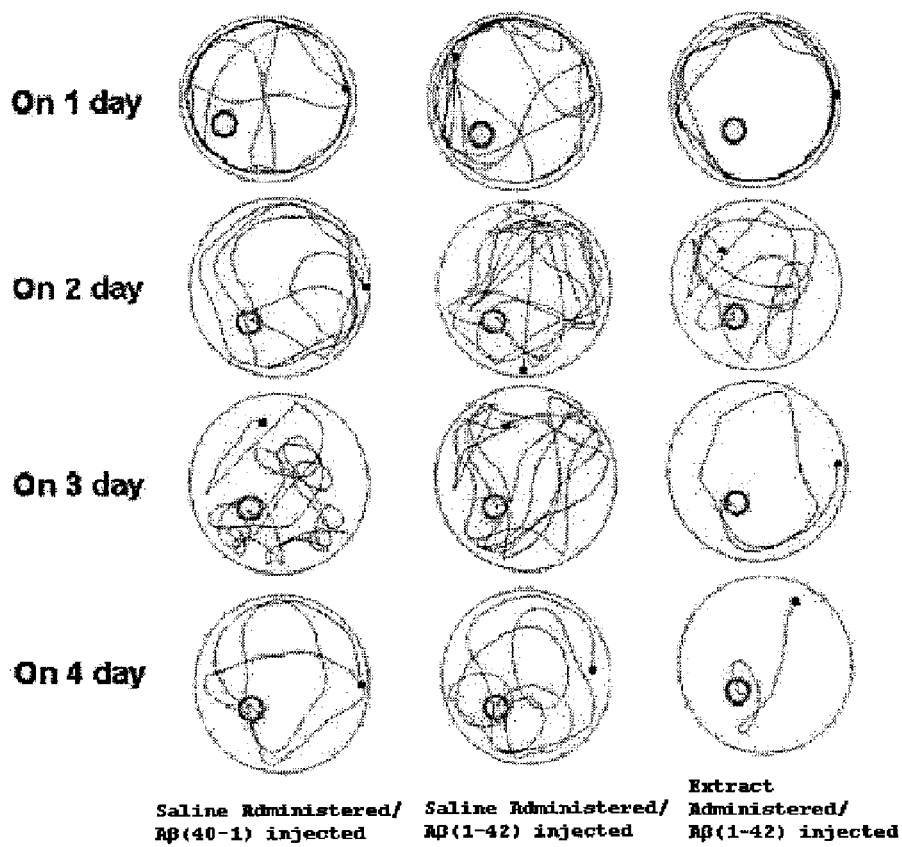
FIG. 2 is a diagram illustrating the tracing patterns of mice in the hidden platform test according to Experimental Example 2.

Further, FIG. 2 illustrates the tracing patterns of the mice during the test above, and the circles therein indicate the location of the platforms. As shown in FIG. 2, in the case of the mice administered with the extract of Example 1, the tracing patterns to locate the platform under water became remarkably simple after 3 days. This shows the learned memory of the mice.

EXPERIMENTAL EXAMPLE 3

Memory Enhancing Effect (Probe Test)

The present test was carried out with the mice in Experimental Example 2, such that the frequency of remembering and passing through the location of the platform under water after removal of the platform was counted. The results of the frequency of passing through the location of the removed platform are shown in Table 2.

TABLE 2

|  | Group administered with saline after Aβ (40-1) injection | Group administered with saline after Aβ (1-42) injection | Group administered with extract after Aβ (1-42) injection |
|---|---|---|---|
| Frequency of passing | 4 to 5 | 2 to 3 | 5 to 7 |

As shown in Table 2, the group administered with the extract of the invention showed a significantly greater frequency of remembering and passing through the location of the removed platform compared with the control group. This proves that the extract of the invention has a memory enhancing effect.

Figure 3:
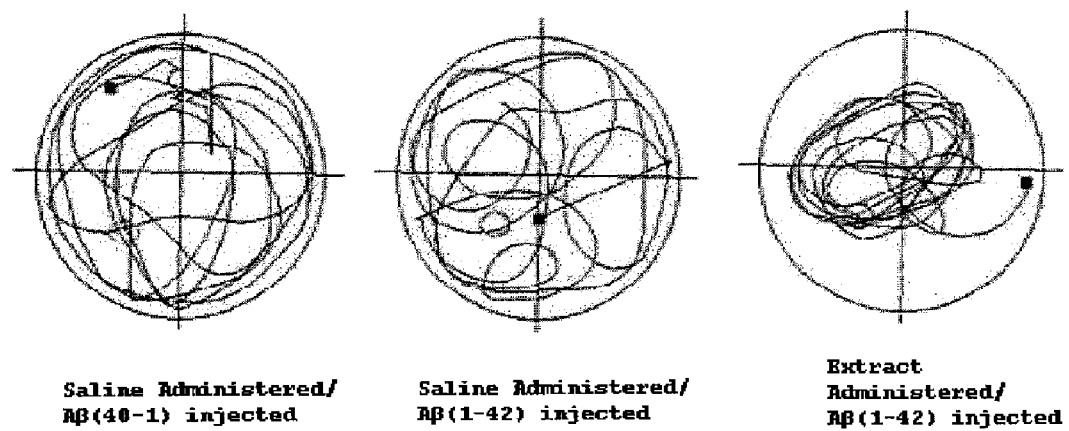
FIG. 3 is a diagram illustrating the tracing patterns of mice in a probe test according to Experimental Example 3.

FIG. 3, in which the tracing patterns of the mice during the present test are illustrated, also shows the same results. It can be clearly seen that the mice of the group administered with the extract of the invention remembered the location where the platform was previously present and showed a pattern of intensive passage through the remembered location.

EXPERIMENTAL EXAMPLE 4

Working Memory Enhancing Effect (Working Memory Test)

A working memory test was carried out for 3 days, in order to measure the time taken to locate the platform when the location of the platform was altered each day.

Figure 4:
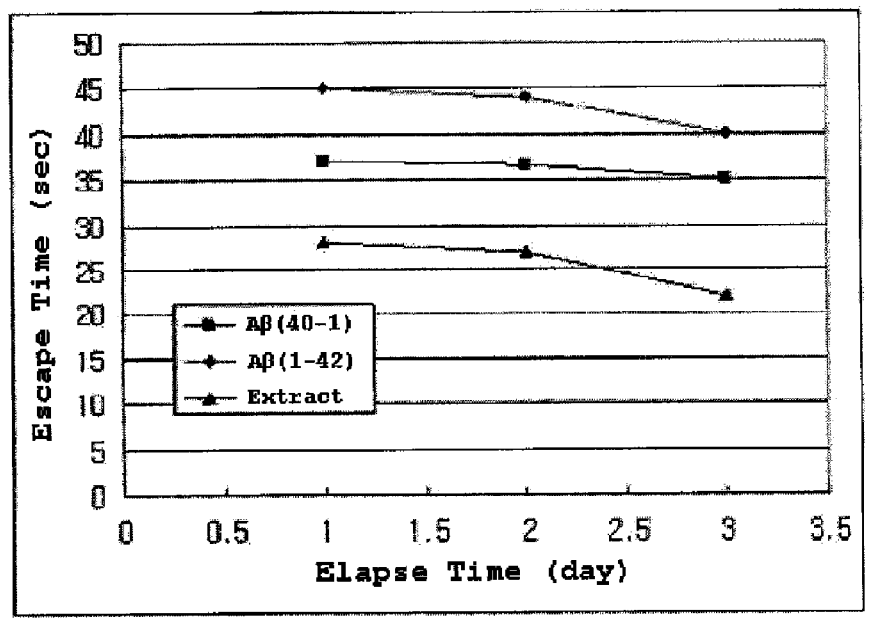
FIG. 4 is a graph showing the results of a working memory test according to Experimental Example 4.

As a result, as shown in FIG. 4, it could be seen that the mice administered with the extract of the invention took significantly shorter time to locate the platform, compared with the mice having no administration.

EXPERIMENTAL EXAMPLE 5

Neural Cell Protective Function

The effect of the extract of Example 1 in the neural cell protective function was evaluated, and as a result, it was found that the extract of the invention had the neural cell protective function to a significant extent, as described in the following.

When a mouse is treated with kainic acid, it suffers from epileptic convulsions and shows a symptom of having the neural cells damaged. Based on this phenomenon, an investigation was carried out with the group administered with the extract of the invention in comparison with the control group, on the expression of the Fos-related antigen (FRA), which is an index for damages in the neural cells. When a comparison in the FRA-immunoreactivity at the dentate gyrus of the cerebrum was made, the group administered with the extract showed a value at least 30% lower than that of the group administered with saline. Therefore, it was found that the extract of the invention had an effect of preventing damages in the neural cells.

As described above, the extract of *Rhus verniciflua* obtained in Example 1 of the invention does not induce allergies upon intake while exhibiting all of the pharmacological effects of *Rhus verniciflua*, so that it can be utilized in various applications for maintaining the human health. In particular, the extract obtained in the method of the invention has superior efficacy for memory enhancement and treatment of senile dementia.

A person having ordinary skill in the art pertinent to the invention will be able to perform various modifications and variances within the scope of the invention, based on the above findings.

INDUSTRIAL APPLICABILITY

As described above, the process for preparing an extract of *Rhus verniciflua* according to the invention enables removal of insoluble impurities and purification of the pharmacologically effective components which are also completely water-soluble, so that the extract obtained thereby preserves the inherent pharmacological efficacy of *Rhus verniciflua*, such as the functions of memory enhancement and dementia treatment, and can be taken without causing any side effects such as allergies. Thus, the extract can be widely used as a raw material of functional foods for health maintenance, medicines and the like.

The invention claimed is:

1. A process for preparing an extract of *Rhus verniciflua* by using water and organic solvents in extraction of the active ingredients of *Rhus verniciflua*, which comprises:
    (a) adding water or a mixture of water and alcohol as a solvent to *Rhus verniciflua* to extract the soluble components, then filtering out the solids to obtain a filtrate, and concentrating and drying the filtrate to obtain a solid fraction;
    (b) re-extracting the solid fraction obtained in the previous step with ethanol having a purity of 95 to 99(%)(v/v), then filtering out the insolubles to obtain a filtrate, and concentrating and drying the filtrate to obtain a solid fraction;
    (c) adding a saturated hydrocarbon having 5 to 7 carbon atoms to the solid fraction obtained in the previous step to dissolve allergy-inducing components, and then removing the hydrocarbon to obtain a solid fraction;
    (d) adding water to the solid fraction obtained in the previous step to extract water-soluble components; and
    (e) adding alumina to the filtrate obtained in the previous step to remove allergy-inducing components by adsorption, filtering the resulting mixture, and then concentrating and freeze-drying the filtrate to obtain a solid fraction.

2. The process according to claim 1, wherein the mixture of water and alcohol used as the solvent in the step (a) contains 0 to 90% by volume of alcohol.

3. The process according to claim 1, wherein the ethanol in the step (b) is added in an amount of 3 to 30 weight-folds with respect to the solid fraction.

4. The process according to claim 1, wherein the hydrocarbon having 5 to 7 carbon atoms in the step (c) is hexane.

5. The process according to claim 4, wherein the hexane is added in an amount of 1 to 30 weight-folds with respect to the solid fraction.

6. The process according to claim 1, wherein the hydrocarbon having 5 to 7 carbon atoms in the step (c) is added in an amount of 1 to 30 weight-folds with respect to the solid fraction.

7. The process according to claim 1, wherein the water in the step (d) is added in an amount of 1 to 50 weight-folds with respect to the solid fraction.

8. The process according to claim 1, wherein said alumina is added in an amount of 1 to 10% (w/v) with respect to the filtrate obtained in the step (d).

9. An extract of *Rhus verniciflua* having a cerebral neural cell protective function, which is prepared by the process according to claim 1 and comprises 1 to 30% by weight of fustin (3,3',4',7-tetrahydroxyflavanone), 0.5 to 20% by weight of fisetin (3,3',4',7-tetrahydroxyflavone), 0 to 5% by weight of sulfuretin (3,4',6-trihydroxyaurone) and 0 to 3% by weight of butein (3,4,2',4-tetrahydroxychalcone).

10. The extract of *Rhus verniciflua* according to claim 9, wherein the extract has a memory enhancing effect.

11. A pharmaceutical composition for memory enhancement, comprising (a) a therapeutically effective amount of the extract according to claim 9 as an active ingredient, and (b) a pharmaceutically acceptable carrier, diluent, excipient or a combination thereof.

12. The pharmaceutical composition according to claim 11, which is used for the purpose of treating dementia.

* * * * *